(12) United States Patent
Hof et al.

(10) Patent No.: US 6,476,231 B2
(45) Date of Patent: Nov. 5, 2002

(54) PROCESS FOR THE PREPARATION OF N-CARBOXY-T-LEUCINE ANHYDRIDE

(75) Inventors: Robert P Hof, Panningen (NL); Wilhelmus Zwaan, Panningen (NL)

(73) Assignee: DSM N.V., Heerlen (NL)

( * ) Notice: Subject to any disclaimer, the term of this patent is extended or adjusted under 35 U.S.C. 154(b) by 0 days.

(21) Appl. No.: 09/852,849

(22) Filed: May 11, 2001

(65) Prior Publication Data

US 2001/0041812 A1 Nov. 15, 2001

(30) Foreign Application Priority Data

May 12, 2000 (NL) .............................................. 1015169

(51) Int. Cl.[7] .............................................. C07D 263/44
(52) U.S. Cl. ........................................ 548/227; 548/215
(58) Field of Search ................................ 548/124, 227, 548/215

(56) References Cited

FOREIGN PATENT DOCUMENTS

GB          1 038 913          8/1966

OTHER PUBLICATIONS

Izumiya et al Journal of Biological Chemistry 1953, 205, pp. 221–230.*

March Advanced Organic Chemistry, 3rd Edition, John Wiley & Sons, New York, 1985, p. 388.*

M. Johnston et al., "A New Approach to the Preparation of N–Carboxy alpha–Amino Acid Anhydrides", Journal of Organic Chemistry, deel 50, nr. 12, 1985, pp. 2200–2202.

* cited by examiner

Primary Examiner—Johann Richter
Assistant Examiner—Paul A. Zucker
(74) Attorney, Agent, or Firm—Pillsbury Winthrop LLP

(57) ABSTRACT

Process for the preparation of N-carboxy-t-leucine anhydride in which the corresponding N-carboxy-t-leucine is subjected to a cyclization with the aid of an acyl halogenide. Preferably, acetyl chloride is used as acyl halogenide. The N-carboxy-t-leucine anhydride obtained optionally is subsequently converted into a t-leucine-N-substituted amide with the aid of the corresponding amine. Preferably, methyl amine is chosen as the amine, and the reaction is carried out in a mixture of water and methanol as solvent.

13 Claims, No Drawings

PROCESS FOR THE PREPARATION OF N-CARBOXY-T-LEUCINE ANHYDRIDE

FIELD OF THE INVENTION

The invention relates to a process for the preparation of an N-carboxy amino acid anhydride in which the corresponding N-carboxy amino acid is subjected to a cyclization with the aid of an acid halogenide.

DESCRIPTION OF THE RELATED ART

Such a process is known for instance from Houben-Weyl, Methoden der Organischen Chemie, Synthese von Peptiden, 4$^{th}$ edition, p. 187 ff., and from Leuchs, H., Berichter der Deutschen Chemische Gesellschaft, 39, 857, 1906.

A drawback of the known process is that such reactions with thionyl chloride are rather violent, as a result of which they are difficult to control in practice. Moreover, thionyl chloride and the $SO_2$ and hydrochloric acid produced during the reaction are corrosive.

Another process is the direct formation of N-carboxy amino acid anhydrides through reaction of amino acids with phosgene. A drawback of this process is the extremely toxic character of phosgene, which sets special demands on the safety precautions during industrial process operation.

SUMMARY OF THE INVENTION

The invention now provides a process for the preparation of N-carboxy-t-leucine anhydride of formula (I) that does not have said drawbacks, there being no need to apply thionyl chloride or phosgene.

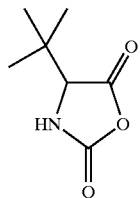

(I)

Applicant now has found that it is possible to prepare N-carboxy-t-leucine anhydride from N-carboxy-t-leucine with the aid of an acyl halogenide.

DETAILED DESCRIPTION OF THE INVENTION

Examples of acyl halogenides that are suitable for use in the process according to the invention are acyl halogenides having the formula R—C(O)—X, where X stands for Cl, Br, I or F, and R stands for an alkyl group or an aryl group with 1–20 carbon atoms, which may be substituted, for instance with an alkyl or aryl group, halogen, hydroxy, alkoxy or amino group. In practice the choice will mostly be determined by the availability and the price of the acyl halogenide. Preferably, therefore, use is made of an acyl chloride, in particular acetyl chloride.

The temperature at which the preparation of the N-carboxy-t-leucine anhydride takes place is not very critical; at a higher temperature the reaction proceeds faster. In practice the reflux temperature is often used. Preferably, the temperature is between 0 and 150° C.

In principle, the conversion with the acyl halogenide is equimolar. The amount of acyl halogenide used in practice is therefore preferably higher than 0.8 equivalents of acyl halogenide, calculated relative to the amount of N-carboxy-t-leucine. When maximum conversion is aimed at, use is preferably made of 1–10 equivalents of acyl halogenide relative to N-carboxy-t-leucine, in particular 1–2 equivalents.

The process preferably takes place in non-protic organic solvents, preferably high-boiling solvents. Examples of suitable organic solvents are hydrocarbons, preferably aromatic hydrocarbons, for instance toluene. The reaction can be carried out at normal, elevated and reduced pressure. Preferably, the reaction is carried out under atmospheric conditions.

The N-carboxy-t-leucine used as starting material in the process according to the invention can be prepared using generally known processes, for instance from t-leucine in a way known for providing such N-protective groups, for instance with the aid of a chloroformic acid ester having the formula Cl—C(O)—OR, where R for instance represents an alkyl group with for instance 1–10 C-atoms or an aryl group with for instance 6–12 C-atoms and is preferably chosen to correspond to the known protecting groups. An example of a suitable choice of R is methyl.

The N-carboxy-t-leucine anhydride obtained according to the invention can suitably be applied in the preparation of substituted amino acid amides, for instance t-leucine-N-substituted amide. To this end, the N-carboxy-t-leucine anhydride is for instance treated with 0.8–5 equivalents, preferably 1–2 equivalents of the corresponding amine. The temperature at which the conversion to the t-leucine-N-substituted amide takes place preferably lies between −10 and 100° C. Preferably, the N-carboxy-t-leucine anphydride is converted into a t-leucine-N-alkylamide (with the alkyl group for instance containing 1–5 carbon atoms), in particular t-leucine-N-methylamide. By way of example the use of an excess of a solution of methylamine in water and/or an alcohol can be mentioned. Preferably, the reaction is carried out in a mixture of water and methanol.

The invention will be elucidated with reference to the examples, without however being restricted by these.

EXAMPLE I

Preparation of L-tert-leucine-N-carboxy anhydride 5.67 g (30 mmol) N-methoxycarbonyl-L-tert-leucine was dissolved in 25 ml toluene. Then 2.59 g acetyl chloride (33 mmol) was added. The mixture was heated for 2 hours at 80° C. The reaction mixture was allowed to stand overnight and was then evaporated to dryness. The solid obtained was recrystallized from a toluene/petroleum ether mixture. Yield: 3.0 g (64%) L-tert-leucine-N-carboxy anhydride.

EXAMPLE II 19.05 g N-methoxycarbonyl-L-tert-leucine (101 mmol) and 100 ml toluene were heated to 80° C. Slowly 8.35 g (107 mmol) acetyl chloride was added to the mixture. The mixture was stirred for 3 hours at 80° C. and then slowly cooled down to room temperature. The solid was isolated by means of filtration and dried. Yield: 10.4 g (65%) L-tert-leucine-N-carboxy anhydride.

EXAMPLE III

Preparation of L-tert-leucine-N-methyl amide 10.9 g (53 mmol) N-methoxycarbonyl-L-tert-leucine, 85 ml toluene and 7 g (106 mmol) acetyl chloride were refluxed for 5.5 hours. The reaction mixture was evaporated to dryness and the residue was dissolved in 40 ml toluene+20 ml methanol. The solution was slowly added to 30 ml of a 40 wt. % solution of methylamine in water+20 ml methanol. After being stirred overnight, the mixture was evaporated to dryness and stripped 3 times with toluene. Yield 7.4 g (51 mmol, 97%) L-tert-leucine-N-methyl amide.

EXAMPLE IV 100 g N-methoxycarbonyl-L-tert-leucine (0.52 mol), 500 ml toluene and 82 g (1.05 mol) acetyl chloride were slowly heated to reflux during a period of 2 hours. The mixture was cooled and evaporated to dryness. 2×110 ml toluene was added, followed by evaporation to dryness. The residue was dissolved in toluene up to a total weight of 325 g. 100 ml methanol was added and the solution was added to 120 ml of a 40 wt. % methyl amine solution in water+300 ml methanol. The mixture was stirred for 1 hour at 0° C. and for 15 minutes at 20° C. The reaction mixture was evaporated to dryness and stripped 3 times with 150 ml toluene. The residue was dissolved in toluene and subsequently 200 ml heptane was slowly added. The solid was isolated via filtration. After drying 66.2 g (0.46 mol, 88%) L-tert-leucine-N-methyl amide was obtained.

What is claimed is:

1. A process which comprises subjecting N-carboxy-t-leucine to a cyclization reaction with an acyl halide to prepare an N-carboxy-t-leucine anhydride of formula (I)

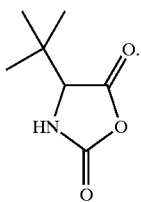

(I)

2. The process of claim 1 wherein the acyl halide is acetyl chloride.

3. The process of claim 1, in which the amount of acyl halogenide to be used ranges from 1.05 to 1.2 equivalents, calculated relative to the amount of N-carboxy-t-leucine.

4. The process of claim 1, in which the reaction is carried out at a temperature between 0 and 150° C.

5. A process which comprises cyclizing N-carboxy-t-leucine with from 1.05 to 1.2 equivalents of acetyl chloride at a temperature of form 0° C. to prepare and N-carboxy-t-leucine anhydride of formula (I)

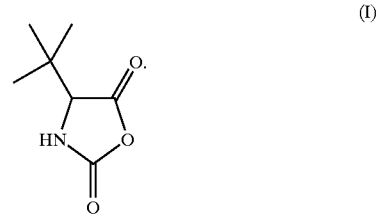

(I)

6. The process of claim 5, wherein the reaction is carried out in a non-protic organic solvent.

7. The process of claim 1, wherein the reaction is carried out in a non-protic organic solvent.

8. The process of claim 6, further comprising reacting the N-carboxy-t-leucine anhydride of formula (I) with an amine to form the corresponding t-leucine-N-substituted amine.

9. The process of claim 1, further comprising reacting the N-carboxy-t-leucine anhydride of formula (I) with an amine to form the corresponding t-leucine-N-substituted amine.

10. The process of claim 9, wherein the amine is methylamine.

11. The process of claim 8, wherein the amine is methylamine.

12. The process of claim 8, wherein the reaction with an amine is carried out in a solvent comprising a mixture of water and methanol.

13. The process of claim 9, wherein the reaction with an amine is carried out in a solvent comprising a mixture of water and methanol.

* * * * *